United States Patent

Mills

[11] Patent Number: 4,933,461
[45] Date of Patent: Jun. 12, 1990

[54] PREPARATION OF A PIPERIDINYLCYCLOPENTYLHEPTENOIC ACID DERIVATIVE

[75] Inventor: Keith Mills, Ware, England

[73] Assignee: Glaxo Group Limited, London, England

[21] Appl. No.: 209,964

[22] Filed: Jun. 21, 1988

[30] Foreign Application Priority Data

Jun. 30, 1987 [GB] United Kingdom ................. 8715333

[51] Int. Cl.$^5$ .......................................... C07D 211/34
[52] U.S. Cl. .................................................. 546/239
[58] Field of Search ........................................ 546/239

[56] References Cited

U.S. PATENT DOCUMENTS

4,342,756  8/1982  Collington et al. ................. 546/239

FOREIGN PATENT DOCUMENTS

| 0234737 | 2/1987 | European Pat. Off. ............ 546/239 |
| 2097397 | 11/1982 | United Kingdom ................ 546/239 |
| 2127406 | 4/1984 | United Kingdom ................ 546/239 |
| 2129796 | 5/1984 | United Kingdom ................ 546/239 |

OTHER PUBLICATIONS

Miyaura et al., Synthetic Communications, 11(7), pp. 513–519, 1981.

*Primary Examiner*—Glennon H. Hollrah
*Assistant Examiner*—Ba K. Trinh
*Attorney, Agent, or Firm*—Bacon & Thomas

[57] ABSTRACT

A process is described for the preparation of a compound of formula (1)

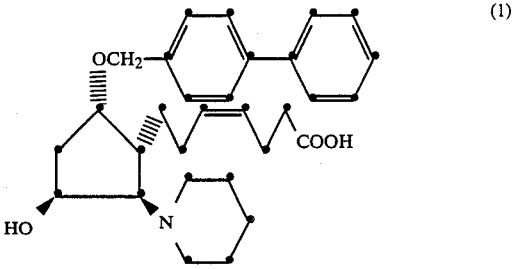

or a salt thereof, which comprises reacting a compound of formula (2)

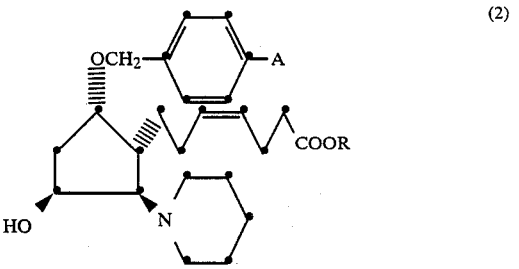

(where A is a displaceable atom or group and R is a hydrogen atom or a $C_{1-6}$alkyl or $C_{7-20}$aralkyl protecting group) or a salt thereof, to replace the moiety A with a phenyl group, followed where necessary by removal of a $C_{1-6}$alkyl or $C_{7-20}$aralkyl protecting group and/or by salt formation. The replacement of A in formula (2) by a phenyl group may be effected with a compound PhX (3) wherein Ph represents a phenyl and X is an atom or group as defined for A in formula (2) or X is a metal atom or metal-containing group or a group $SiR'_3$ (where R' is an alkyl or aryl group) provided that when A is —B(OH)$_2$ X can only represent a conventional leaving group.

8 Claims, No Drawings

PREPARATION OF A PIPERIDINYLCYCLOPENTYLHEPTENOIC ACID DERIVATIVE

This invention relates to a new process for the preparation of [1R[1α(Z),2β,3β,5α]]-(+)-7-[5-[[(1,1'-biphenyl)-4-yl]methoxy]-3-hydroxy-2-(1-piperidinyl)-cyclopentyl]-4-heptenoic acid and salts thereof.

In GB-A No. 2097397, GB-A No. 2127406, GB-A No. 2129796 and EP-A No. 234737 we describe inter alia [1R-[1α(Z),2β,3β,5α]]-(+)-7-[5-[[(1,1'-biphenyl)-4-yl]methoxy]-3-hydroxy-2-(1-piperidinyl)cyclopentyl]-4-heptenoic acid and salts thereof and methods for their preparation. The compound and its salts, e.g. the hydrochloride salt, are potent antagonists of the actions of thromboxane $A_2$ and, in particular, inhibit thromboxane $A_2$ and endoperoxide mediated aggregation of blood platelets.

[1R-[1α(Z),2β,3β,5α]]-(+)-7-[5-[[(1,1'-biphenyl)-4-yl]methoxy]-3-hydroxy-2-(1-piperidinyl)cyclopentyl]-4-heptenoic acid may be represented by formula (1):

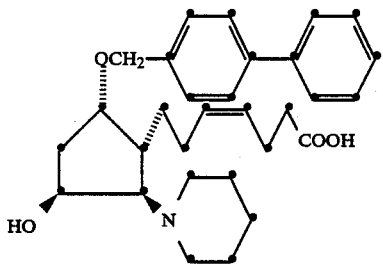

(1)

Formula (1) and the various other formulae used herein, with the exception of formulae (3), (13) and (14), are to be understood to relate to the 1R enantiomers of the compounds concerned.

We have now found a new and convenient process for the preparation of the compound of formula (1) and its salts. The new process is particularly convenient because it involves a simple displacement reaction and may provide the desired compound in excellent yield. Thus, in one aspect of the present invention, we provide a process for the preparation of the compound of formula (1) and salts thereof which comprises reacting a compound of formula (2)

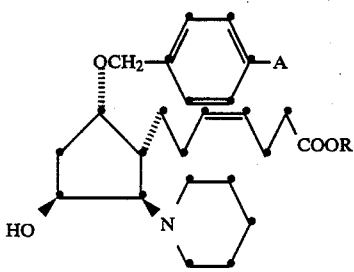

(2)

(where A is a displaceable atom or group and R is a hydrogen atom or a $C_{1-6}$ alkyl or $C_{7-20}$ aralkyl protecting group) or a salt thereof, to replace the moiety A with a phenyl group, followed where necessary by removal of a $C_{1-6}$ alkyl or $C_{7-20}$ aralkyl protecting group and/or by salt formation.

Displaceable atoms or groups represented by the moiety A include any conventional leaving group such as halogen (e.g. chlorine, bromine or iodine), triflate or a phosphate ester (e.g. diethylphosphate) or A may represent a group $-B(OH)_2$. When R is a $C_{1-6}$ alkyl group it may be, for example, methyl, ethyl or t-butyl. When R is a $C_{7-20}$ aralkyl group it may be, for example, benzyl, benzhydryl or trityl. Suitable salts of a compound of formula (2) for use according to the present invention include any of the salts referred to in the aforementioned British and European patent specifications. However, the hydrochloride salt is preferred.

Replacement of the moiety A by a phenyl group may be effected by a coupling reaction of a compound of formula (2) or a salt thereof with a compound of formula (3)

PhX (3)

[where Ph represents phenyl and X is an atom or group as defined above for A or X is a suitable metal atom or metal-containing group such as Li, Cu, MgHal, ZnHal, HgHal or $SnR'_3$ or X is a group $SiR'_3$ (wherein Hal is a halogen atom, e.g. chlorine, bromine or iodine, and R' is a $C_{1-6}$ alkyl group, e.g. methyl or n-butyl, or an aryl group, e.g. phenyl)] with the proviso that when A in formula (2) represents a group $-B(OH)_2$ then X in formula (3) may only represent a conventional leaving group such as halogen. It is to be understood that when X represents MgHal or Li then the moiety R in formula (2) may not represent a protecting group.

In a preferred embodiment of the present process, compounds of formulae (2) and (3) are reacted wherein one of A and X represents a halogen atom (e.g. bromine) and the other represents a group $-B(OH)_2$. The coupling reaction may conveniently be carried out in the presence of a suitable transition metal catalyst such as a palladium (0) or palladium (II) catalyst, for example $PdL_4$ or $PdCl_2L_2$ (where L is a phosphine ligand such as triphenylphosphine or tritolylphosphine) in a suitable solvent such as an ether (e.g. 1,2-dimethoxyethane or tetrahydrofuran), a hydrocarbon, for example an aromatic hydrocarbon (e.g. benzene), or a dipolar aprotic solvent such as N,N-dimethylformamide containing an appropriate base which may be, for example, a carbonate, bicarbonate or hydroxide of an alkali or alkaline earth metal (e.g. aqueous sodium carbonate) or a suitable amine such as a tertiary amine (e.g. triethylamine). The reaction may be effected at any suitable temperature up to and including reflux, for example in the range 20°–120° C. and preferably in the range 60°–80° C. Ultrasonic techniques or microwave may also be used to facilitate the reaction. The coupling reaction is preferably carried out in the presence of the catalyst $(Ph_3P)_4Pd$.

When A and X in formulae (2) and (3) are conventional leaving groups as defined for A in formula (2) the coupling reaction may be carried out in a single step in the presence of a suitable transition metal catalyst (e.g. a palladium or nickel catalyst) and under reducing conditions (e.g. using a reducing agent such as zinc metal or hydrazine or by electrolytic reduction). Suitable palladium catalysts include palladium-on-charcoal, a palladium (II) chloride-mercury (II) chloride couple, $PdL_4$ and $PdCl_2L_2$ (where L is as defined above). Suitable nickel catalysts include nickel (II) chloride and $NiCl_2L_2$ (where L is as defined above). The specific conditions for effecting the desired conversion will, of course, depend on the particular values of A and X in formulae (2) and (3) respectively. However, the conditions referred to in the following publications may be suitable for present purposes: Chem. Letters 1986, p. 407; J. Org. Chem. 1986, p. 2627; Tetrahedron Letters 1977, p. 4089; Synthesis 1978, p. 537; Bull. Chem. Soc. Japan 1980, 53, p. 1767 and Tetrahedron Letters 1985, p. 1655.

When X in formula (3) is a conventional leaving group as defined for A in formula (2), the compound of formula (2) may first be converted to a compound of formula (4)

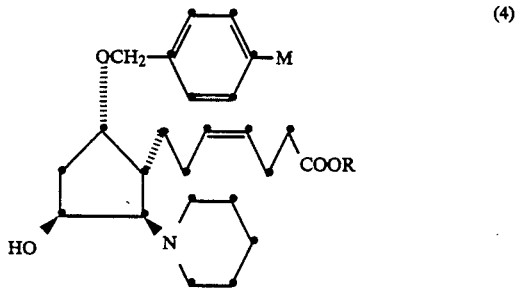

(4)

[where R is as previously defined and M is a suitable atom or metal-containing group such as Li, Cu, MgHal, ZnHal, HgHal or SnR'$_3$ or X is a group SiR'$_3$ (wherein Hal and R' are as previously defined)] and then the compound of formula (4) reacted with an appropriate compound of formula (3) to give the desired product. It is to be understood that when M represents MgHal or Li then the moiety R in formula (4) may not represent a protecting group.

Compounds of formula (4) may be prepared by treating a compound of formula (2) in which A represents a conventional leaving group such as halogen (e.g. chlorine or, more especially, bromine or iodine), triflate or a phosphate ester (e.g. diethylphosphate) with a reagent capable of introducing the moiety M. Suitable reagents and conditions for effecting the desired conversion are known in the art (cf. J. Am. Chem. Soc. 1987, p. 8056; J. Org. Chem. 1984, p. 5280; Chem. Letters 1981, p. 829; J. Organometal. Chem. 1983, p. 551; Tetrahedron Letters 1987, p. 4715 and Tetrahedron Letter 1983, p. 4895). Thus, for example, a compound of formula (4) in which M is ZnHal may be prepared from a corresponding halo compound of formula (2) in which A is a halogen atom (e.g. bromine or iodine) by reaction with activated zinc. A compound of formula (4) in which M is Cu may be prepared from a corresponding halo compound of formula (2) in which A is a halogen atom (e.g. bromine or iodine) by reaction with Riecke copper. A compound of formula (4) in which M is MgHal may be prepared from a corresponding halo compound of formula (2) in which A is a halogen atom (e.g. bromine or iodine) by reaction with magnesium or with MgHal$_2$ (where Hal is as defined above) in the presence of lithium. A compound of formula (4) in which M is Li may be prepared from a corresponding halo compound of formula (2) in which A is a halogen atom (e.g. bromine or iodine) by reaction with a suitable organolithium reagent (e.g. n-butyllithium). A compound of formula (4) in which M is SnR'$_3$ or SiR'$_3$ may be prepared from a corresponding compound of formula (2) in which A is a conventional leaving group such as a halogen atom (e.g. bromine or iodine), triflate or phosphate ester (e.g. diethylphosphate) by reaction with either R$_3$'Sn-SnR'$_3$ or R'$_3$Si-SiR'$_3$ in the presence of a suitable palladium catalyst. Alternatively, Al(SiR'$_3$)$_3$ and a catalyst NiCl$_2$L$_2$ (where R' and L are as defined above) may be used to prepare a compound of formula (4) in which M is SiR'$_3$.

The resulting compound of formula (4) is then treated with a compound of formula (3) in which X is a conventional leaving group such as halogen (e.g. bromine or iodine), triflate or a phosphate ester (e.g. diethylphosphate). The coupling reaction may conveniently be effected in the presence of a suitable transition metal catalyst such as a palladium or nickel catalyst (e.g. PdL$_4$, PdCl$_2$L$_2$, NiCl$_2$ or NiCl$_2$L$_2$, where L is as defined previously) in a suitable solvent such as an ether (e.g. diethyl ether, tetrahydrofuran or 1,2-dimethoxyethane), hexamethylphosphoramide, dimethylformamide, dioxane, acetonitrile or an aromatic hydrocarbon (e.g. benzene). The specific conditions for effecting the desired reaction will, of course, depend on the particular values of M and X in formulae (4) and (3) respectively. However, the conditions referred to in the following publications may be suitable for present purposes: Comprehensive Organometal. Chem. volume 8, p. 910; Current Trends in Organic Synthesis (Pergamon Press 1982) p. 269; J. Am. Chem. Soc. 1941, 63, p. 2316; J. Organometal. Chem. 1984, 267, Cl; J. Am. Chem. Soc. 1987, 109, p. 5479; J. Org. Chem. 1983, p. 1333; Tetrahedron Letters 1986, p. 4407; J. Am. Chem. Soc. 1979, 101, p. 4992 and J. Organometal. Chem. 1983, 250, p. 551.

When X in formula (3) is a metal or metal-containing group as defined previously, the coupling reaction may be carried out with a compound of formula (2) in which A is a conventional leaving group as defined above in a single step using the conditions described above for the coupling of compounds of formulae (3) and (4).

It is to be understood that the use of stoichiometric amounts of the transition metal "catalyst" may be advantageous in some of the aforementioned coupling reactions.

It will be appreciated that certain of the aforementioned coupling reactions may only be applied to compounds of formulae (2) and (4) in which R is a C$_{1-6}$ alkyl or C$_{7-20}$ aralkyl protecting group. In these situations conversion to the desired compound of formula (1) or a salt thereof may be effected subsequent to the coupling reaction by deprotection using conventional means (e.g. by acid or base hydrolysis) followed, if necessary, by salt formation. Thus, according to another particular aspect of the present invention we provide a process for the preparation of the compound of formula (1) or a salt thereof which comprises the steps of (i) reacting a compound of formula (2) in which A is a displaceable atom or group and R is a C$_{1-6}$ alkyl or C$_{7-20}$ aralkyl protecting group or a salt thereof to replace the moiety A with a phenyl group to form the ester (5)

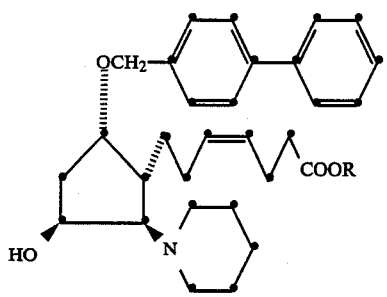

(5)

or a salt thereof (where R is as just defined above) and (ii) hydrolysing the said ester or a salt thereof to obtain the acid of formula (1) and optionally treating said acid to obtain a salt thereof. This two-step process may be particularly convenient when using an intermediate of formula (2) in which A is a halogen atom (e.g. bromine).

If desired, the acid of formula (1) may be isolated in the form of a salt, for example, an acid addition salt such as the hydrochloride salt, by reacting the free base of the acid of formula (1) with an appropriate acid e.g. the hydrochloric acid, for example using the conditions described in GB-A No. 2097397 and GB-A No. 2127406.

The compounds of formula (2) in which R is a hydrogen atom may similarly be prepared from the corresponding esters of formula (2) in which R is a $C_{1-6}$ alkyl or $C_{7-20}$ aralkyl group by conventional acid or base hydrolysis.

The compound of formula (2) in which R is a hydrogen atom and A is a group $—B(OH)_2$ may be prepared by treating a compound of formula (2) in which A is a halogen atom (e.g. bromine) and R is a hydrogen atom at low temperature (e.g. $-100°$ to $-70°$ C.) with a suitable boron reagent such as tri-isopropylborate and an organolithium reagent (e.g. n-butyllithium) in a solvent such as an ether (e.g. tetrahydrofuran). The above conditions may yield the desired boronic acid or the corresponding boronic acid anhydride. If the anhydride is prepared then this compound may be used in the coupling reaction; the corresponding boronic acid may then be formed in situ under the conditions of the coupling reaction.

The compounds of formula (2) in which A is a group $—B(OH)_2$ and R is a $C_{1-6}$ alkyl or $C_{7-20}$ aralkyl group may be prepared from the corresponding acids of formula (2) in which R is a hydrogen atom by conventional esterification procedures.

The compounds of formula (2) in which A is a halogen atom (e.g. bromine) and R is a $C_{1-6}$ alkyl or $C_{7-20}$ aralkyl group may be prepared by the following reaction sequence:

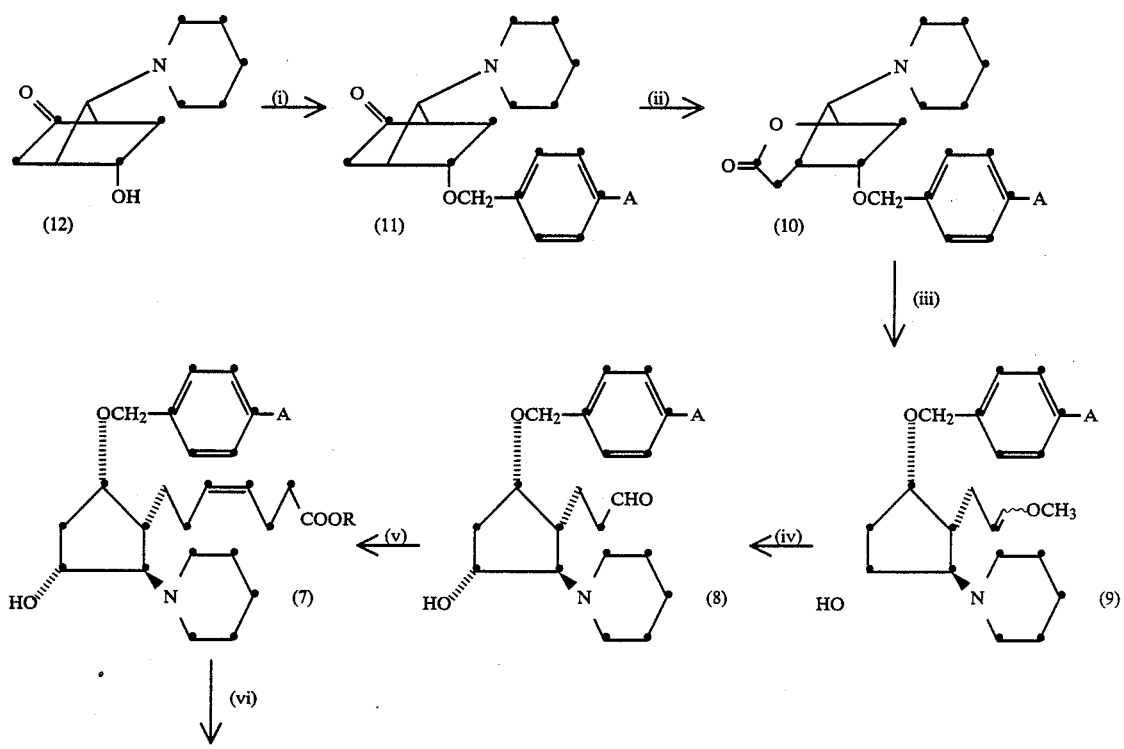

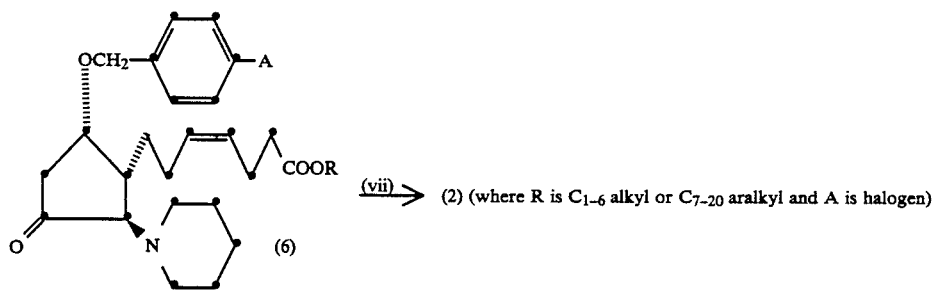

(vii) → (2) (where R is $C_{1-6}$ alkyl or $C_{7-20}$ aralkyl and A is halogen)

Steps (i)-(vi) may be carried out using reaction conditions similar to those described in GB-A No. 2075503. Thus, step (i) may be effected by reacting the known compound (12) with a reagent

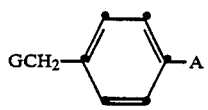

(where G is a leaving group e.g. halogen) under standard alkylation conditions and, if desired, in the presence of a phase transfer catalyst. Step (ii) is a Baeyer-Villiger oxidation to form the lactone (10). Step (iii) involves reduction (e.g. using diisobutyl aluminium hydride) to give the corresponding lactol which is treated with an appropriate Wittig reagent e.g. a phosphorane of formula $CH_3OCH=PPh_3$ (where Ph is phenyl) to give the enol ether (9). Step (iv) involves hydrolysis (e.g. acid hydrolysis using a mineral acid such as hydrochloric acid) to give the aldehyde (8). Step (v) may be effected by treating the aldehyde (8) with an appropriate Wittig reagent e.g. a phosphorane of formula $Ph_3P=CHCH_2CH_2CO_2H$ or a salt thereof, e.g. the potassium salt followed by esterification (e.g. using an alcohol ROH) to give a compound (7) in which R is a $C_{1-6}$ alkyl (e.g. methyl) or $C_{7-20}$ aralkyl group. Step (vi) involves oxidation using a suitable oxidising system e.g. dimethyl sulphoxide activated by a suitable electrophilic reagent (such as oxalyl chloride). Step (vii) may be carried out using a variety of reducing systems and conveniently using the general conditions described in EP-A No. 234737. Thus, reduction may be effected using a borohydride reducing agent (e.g. sodium borohydride) in the presence of a lanthanide (e.g. cerium trichloride).

Intermediates of formula (2) in which A is a displaceable atom or group other than halogen or —B(OH)$_2$ may generally be prepared by methods similar to those described above for preparing corresponding intermediates of formula (2) in which A is halogen or —B-(OH)$_2$.

The compounds of formulae (2) and (4) and the aforementioned boronic acid anhydride and salts thereof are novel intermediates and form a further aspect of the present invention. Particular intermediates of interest are compounds of formula (2), especially those in which A is a halogen (e.g. bromine) atom or a group —B-(OH)$_2$, and salts thereof.

Intermediates of formula (3) are known compounds or can be prepared from known compounds using methods analogous to those used to prepare the known compounds of formula (3).

The intermediate of formula (3) in which X is a group —B(OH)$_2$, i.e. benzeneboronic acid, may be prepared from the corresponding anhydrides of formula (13) or (14) under the conditions of the coupling reaction described hereinbefore involving benzeneboronic acid.

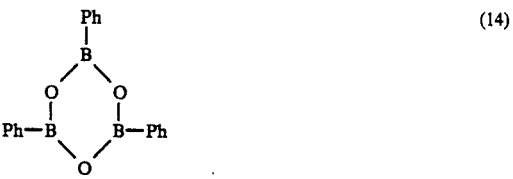

The compounds of formulae (13) and (14) are known classes of compounds described by H. R. Snyder et. al. in J. Am. Chem. Soc., 1958, 80, p. 3611 and F. R. Bean et. al. in J. Am. Chem. Soc., 1932, 54, p. 4415.

The following Intermediates and Examples are included by way of illustration of the invention and should not be construed as a limitation of the invention. All temperatures are in °C. In the following, dired, refers to drying with magnesium sulphate, t.l.c. means thin layer chromatography and NH$_3$ means 0.880 ammonia.

INTERMEDIATE 1

[1R-(endo,anti)]-(+)-5-[(4-Bromophenyl)methoxy]-7-(1-piperidinyl)bicyclo[2.2.1]heptan-2-one, ethanedioate A mixture of [1R-(endo, anti)]-(+)-5-hydroxy-7-(1-piperidinyl) bicyclo[2.2.1]heptan-2-one (50 g), 4-bromobenzyl bromide (100 g), aqueous sodium hydroxide (70%; 125 ml), benzyltriethylammonium chloride (5.5 g) and dichloromethane (750 ml) was stirred vigorously for 48 h. The mixture was diluted with water (600 ml) and the aqueous layer extracted with dichloromethane (200 ml). The combined organic layer was washed with 0.4N (hydrochloric acid (150 ml) and the aqueous acid layer extracted with dichloromethane (100 ml). The combined dichloromethane solutions were washed with 8% sodium bicarbonate and dried. A solution of anhydrous oxalic acid (22.5 g) and water (8 ml) in acetone (350 ml) was then added over 3 min and the mixture seeded. When precipitation was complete the product was filtered off and washed with a mixture of dichloromethane and acetone (4:1; 500 ml) to give the *title compound* (91 g) as cream crystals m.p. 146°-8°. $[\alpha]_D^{20°}$ +16° (1.02% in methanol).

INTERMEDIATE 2

[1R-endo, anti)]-(−)-6-[(4-Bromophenyl)methoxy]-8-(1-piperidinyl)-2-oxabicyclo[3.2.1]octan-3-one Intermediate 1 (62.5 g) was partitioned between aqueous potassium carbonate (8%; 500 ml) and dichloromethane (150 ml; 2×70 ml). Evaporation of the dried extract gave the free base as an orange oil. The oil was dissolved in a mixture of dichloromethane (300 ml), water (100 ml) and sulphuric acid (2N; 69 ml) and peracetic acid (ca 38%; 120 ml) added over 4.5 h with stirring and water bath cooling. The mixture was then stirred at room temperature for 46 h. The mixture was then added over 80 min to a stirred solution of sodium sulphite (250 g) in water (1.3 l). After a further 45 min, sodium metabisulphite (100 g) was added and the mixture stirred vigorously for 5 h. The mixture was cooled in ice and approximately neutralised with 70% sodium hydroxide then basified (pH 8.5–9) with solid potassium carbonate. The aqueous layer was extracted with dichloromethane (3×250 ml) and the combined organic layers dried and evaporated in vacuo to leave a brown gum. Chromatography on silica gel (Merck 7734; 460 g) eluting with dichloromethane (1.8 l) then dichloromethane-ether (4:1) gave a cream solid. Crystallisation from isopropanol (50 ml) gave the *title compound* (27.9 g) as cream crystals m.p. 85°–8°. $[\alpha]_D^{20°}$ −33.5° (0.746% in methanol), −20.6° (0.693% in chloroform).

Analysis Found: C,57.9; H,6.2; N,3.7; $C_{19}H_{24}BrNO_3$ requires C,57.9; H,6.1; N,3.55%.

INTERMEDIATE 3

[1R-(1α, 2β,3α,4α]-(+)-4-[(4-Bromophenyl)methoxy]-3-(3-methoxy-2-propenyl)-2-(1-piperidinyl)cyclopentanol (i) [1R-(endo, anti)]-6-[(4-Bromophenyl)methoxy]-8-(1-piperidinyl)-2-oxabicyclo[3.2.1]octan-3-ol Diisobutyl aluminium hydride (1M in hexane, 60 ml) was added over 30 min (internal temp. kept below −73°) to a stirred cooled (dry ice-acetone) solution of Intermediate 2 (6.8 g) in dichloromethane (150 ml) under nitrogen. After a further 1.5 h, methanol (100 ml) was added, keeping the temperature below −70°. The cooling bath was then removed and the mixture stirred for 2.5 h. The precipitate was filtered off and washed well with dichloromethane-methanol (1:1; 400 ml). The filtrate was evaporated in vacuo, the residue re-dissolved in dichloromethane and the solution stirred with anhydrous magnesium sulphate. The solid was filtered off and the filtrate evaporated in vacuo to give the *title compound* as a yellow gum (7.35 g). T.l.c. (silica/ether) Rf ca. 0.1 (streak).

(ii) [1R-(1α, 2β, 3α, 4α)]-(+)-4-[(4-Bromophenyl)methoxy]-3-(3-methoxy-2-propenyl)-2-(1-piperidinyl)cyclopentanol A Wittig reagent was prepared from methoxymethyltriphenylphosphonium chloride (25.8 g) and potassium tert-butoxide (8.4 g) in dry tetrahydrofuran (170 ml) under nitrogen at 0°. A solution of the product from stage (i) (7.2 g) in tetrahydrofuran (60 ml) was added over 15 min, and the solution stirred at 0° for 2.5 h. Water (20 ml) was added and the solvent removed in vacuo to leave a yellow oil. The oil was diluted with water (400 ml) and extracted with ethyl acetate (150 ml, 2×100 ml). Evaporation of the dried extract gave an orange oil. Chromatography on silica gel (Merck 7734; 500 g) eluting with ethyl acetate (1 l) then ethyl acetate-methanol [(95:5, 1 l), (90:10, 1 l) then (80:20,1 l)] gave an orange oil. The oil was dissolved in ether (50 ml) and insoluble material filtered off. Evaporation of the ether in vacuo left the *title compound* (5.83 g) as a yellow oil. $[\alpha]_D^{20°}$ +40.8° (0.957% in methanol).

Analysis Found: C,59.4; H,7.0; N,3.3; $C_{21}H_{30}BrNO_3$ requires C,59.4; H,7.1; N,3.3%.

INTERMEDIATE 4

[1R-(1α,2β,3α,5α)]-(+)-5-[(4-Bromophenyl)methoxy]-3-hydroxy-2-(1-piperidinyl)cyclopentanepropanal A solution of Intermediate 3 (5.63 g) in a mixture of acetone (40 ml) and hydrochloric acid (2N; 25 ml) was stirred under nitrogen for 2 h. The mixture was diluted with sodium carabonate (0.5N, 300 ml) and the product extracted into dichloromethane (3×50 ml). Evaporation of the dried extract gave the *title compound* (5.48 g) as a light yellow gum. $[\alpha]_D^{20°}$ +34.7° (0.831% in methanol).

Analysis Found: C,58.2; H,7.2; N,3.2; $C_{20}H_{28}BrNO_3$ requires C,58.5; H,6.9; N,3.4%.

INTERMEDIATE 5

[1R-[1α(Z),2β,3α,5α]]-(+)-Methyl7-[5-[(4-bromophenyl)methoxy]-3-hydroxy-2-(1-piperidinyl)cyclopentyl]-4-heptenoate A Wittig reagent was prepared from 3-carboxypropyl triphenylphosphonium bromide (27.1 g) and potassium tert-butoxide (14.6 g) in dry tetrahydrofuran (350 ml) under nitrogen. A solution of Intermediate 4 (5.3 g) in tetrahydrofuran (50 ml) was added over 15 min and the mixture stirred a further 2.5 h. Water (10 ml) and methanol (10 ml) were added and the solvent removed in vacuo. The residue was diluted with water (200 ml) and washed with ether (2×150 ml). The aqueous solution was adjusted to pH 7.5–8.0 and extracted with dichloromethane (6×50 ml) then the pH lowered to 7.0 and further extracted with dichloromethane (4×50 ml). Evaporation of the dried combined extracts gave a yellow foam. The foam was dissolved in methanol (150 ml) and concentrated sulphuric acid (15 ml) added with ice cooling. The solution was then stirred at room temperature for 1.75 h. The mixture was diluted with ice cold aqueous potassium carbonate (140 g in 1.5 l) and extracted with dichloromethane (4×100 ml). Evaporation of the dried extract gave a yellow oil. Chromatography on silica gel (Merck 7734; 440 g), eluting with ethyl acetate (1.5 l), ethyl acetate-methanol [(98:2, 1 l), (95:5, 1 l), (90:10, 1.5 l) then (80:20; 0.5 l)] then ethyl acetate-methanol-triethylamine (79:20:1) gave the *title compound* (4.29 g) as an orange oil. $[\alpha]_D^{20°}$ +4.9° (0.864% in methanol).

Analysis Found: C,60.9; H,7.2; N,3.0; $C_{25}H_{36}BrNO_4$ requires C,60.7; H,7.3; N,2.8%.

INTERMEDIATE 6

[1R-[1α(Z),2β,5α]]-(−)-Methyl7-[5-[(4-bromophenyl)methoxy]-3-oxo-2-(1-piperidinyl)cyclopentyl]-4-heptenoate A solution of dimethylsulphoxide (0.25 ml) in dichloromethane (8 ml) was added, over 5 min, to a stirred, cooled (−78°) solution of oxalyl chloride (0.26 ml) in dichloromethane (10 ml) under nitrogen. After 25 min, a solution of Intermediate 5 (0.98 g) in dichloromethane (12 ml) was added over 5 min. After a further 40 min, triethylamine (1.4 ml) was added, the cooling bath removed and the mixture allowed to warm to room temperature over 45 min. The mixture was diluted with dichloromethane (100 ml) and the solution was washed with aqueous citric acid (10%, 50 ml) and water (50 ml), dried and evaporated in vacuo to leave a yellow oil. Chromatography on silica gel (Merck 7734; 70 g), set up in ether:triethylamine (99:1), eluting with ether gave the *title compound* (0.92 g) as a pale yellow oil. $[\alpha]_D^{20°} -7.0°$ (0.514% in methanol).

Analysis Found: C,61.2; H,7.2; N,3.1; $C_{25}H_{34}BrNO_4$ requires C,61.0; H,7.0; N,2.8%.

INTERMEDIATE 7

[1R-[1α(Z),2β,3β,5β]]-(+)-Methyl7-[5-[(4-bromophenyl)methoxy]-3-hydroxy-2-(1-piperidinyl)cyclopentyl]-4-heptenoate A solution of cerium (III) chloride heptahydrate (0.5 g) in methanol (4 ml) was added to a stirred, cooled (−12°) solution of Intermediate 6 (0.598 g) in methanol. After 1 min., sodium borohydride (0.037 g) was added in three portions over 1 min. After a further 10 min, the mixture was diluted with sodium carbonate (0.2N; 200 ml) and extracted with dichloromethane (4×30 ml). Evaporation of the dried extract gave a colourless oil. Chromatography on silica gel (Merck 7734; 65 g) set up in ether:triethylamine (99:1), eluting with ether:triethylamine (99.9:0.1) gave the *title compound* (0.500 g) as a pale yellow oil. $[\alpha]_D^{20°} +76°$ (0.91% in methanol).

Analysis Found: C,61.1; H,7.7; N,3.0; $C_{25}H_{36}BrNO_4$ requires C,60.7; H,7.3; N,2.8%.

INTERMEDIATE 8

[1R-[1α(Z),2β,3β,5α]]-(+)-7-[5-[(4-Bromophenyl)methoxy]-3-hydroxy-2-(1-piperidinyl)cyclopentyl]-4-heptenoic acid, hydrochloride A solution of Intermediate 7 (0.61 g) in ethanol (12 ml) and aqueous sodium hydroxide (5N; 2.5 ml) was stirred under nitrogen for 3 h. The ethanol was removed in vacuo, the residue made up to 20 ml with water then acidified (pH<1) with concentrated hydrochloric acid and extracted with dichloromethane (3×20 ml). Evaporation of the dried extract gave a cream foam, which was crystallised from dichloromethane-ethyl acetate to give the *title compound* (0.537 g) as white crystals m.p. 145°-7°. $[\alpha]_D^{20°} +60°$ (0.571% in methanol).

Analysis Found: C,55.7; H,6.8; N,2.6; $C_{24}H_{34}BrNO_4$ requires C,55.8; H,6.8; N,2.7%.

INTERMEDIATE 9

[1R-[1α(Z),2β,3β,5α]]-(+)-7-[5-[(4-Boronophenyl)methoxy]-3-hydroxy-2-(1-piperidinyl)cyclopentyl]-4-heptenoic acid n-Butyl lithium (1.55M in hexane; 8.2 ml) was added over 7 min, under nitrogen, to a stirred solution of Intermediate 8 (0.529 g) in a mixture of dry tetrahydrofuran (50 ml) and triisopropyl borate (4.5 ml) at −100°. After a further 10 min at −100°, the mixture was allowed to warm to −70° over 25 min, the cooling bath was then removed and the mixture was kept overnight at room temperature. Methanol (20 ml) and water (2 ml) were added and the mixture evaporated to dryness in vacuo. The residue was chromatographed (silica) eluting with dichloromethane:ethanol:$NH_3$ (100:40:10) to give a gum. The gum was evaporated with ethanol (10 ml) then foamed with water (1 ml) in vacuo to give the *title compound* (0.377 g) as a white solid.

Analysis Found: C,64.3; H,8.3; N,3.1; $C_{24}H_{36}BNO_6$ requires C,64.7; H,8.15; N,3.15%.

T.l.c. (silica) dichloromethane:ethanol:methanol:ammonium hydroxide (100:40:40:2) Rf 0.19.

EXAMPLE 1

[1R-[1α(Z),2β,3β,5α]]-(+)-7-[5-[[(1,1'-Biphenyl)-4-yl]methoxy]-3-hydroxy-2-(1-piperidinyl)cyclopentyl]-4-heptenoic acid, hydrochloride A mixture of Intermediate 9 (0.1 g), bromobenzene (0.112 g), tetrakis(triphenylphosphine)palladium (0) (0.015 g), aqueous sodium carbonate (2N; 1.5 ml) and 1,2-dimethoxyethane (4 ml) was stirred at reflux under an atmosphere of nitrogen for 3 h. The mixture was diluted with sulphuric acid (2N; 1.5 ml) and pH 6.5 phosphate buffer (30 ml), and extracted with dichloromethane. Evaporation of the dried extract gave a yellow gum which was chromatographed (silica) eluting with dichloromethane:ethanol:$NH_3$ (86:16:2) to give a cream solid. This solid was dissolved in dichloromethane and excess ethereal hydrogen chloride and ether were added. The precipitate that formed was triturated with ether to give a solid which was crystallised from a mixture of methanol and ethyl acetate to give the *title compound* as a white solid (35 mg) which did not depress the melting point of an authentic sample of Example 1 of GB-A No. 2127406.

EXAMPLE 2

[1R-[1α(Z),2β,3β,5α]]-(+)-7-[5-[[(1,1'-Biphenyl)-4-yl]methoxy]-3-hydroxy-2-(1-piperidinyl)cyclopentyl]-4-heptenoic acid, hydrochloride A mixture of Intermediate 8 (0.1 g), benzeneboronic acid (40 mg), tetrakis(triphenylphosphine)palladium(0) (15 mg), aqueous sodium carbonate (2N; 1.5 ml) and 1,2-dimethoxyethane (5 ml) was stirred at reflux under an atmosphere of nitrogen for 6 h. Hydrochloric acid (1N; 25 ml) was added and the mixture extracted with dichloromethane. The extract was evaporated in vacuo and the residue was washed with ether to leave a yellow gum which was chromatographed (silica), eluting with dichloromethane:ethanol:$NH_3$ (86:16:2) to give a white foam. This foam was dissolved in dichloromethane and excess ethereal hydrogen chloride and ether were added. The precipitate that formed was triturated with ether to give a solid which was crystallised from a mixture of methanol and ethyl acetate to give the *title compound* as a white solid (40 mg) which did not depress the melting point of an authentic sample of Example 1 of GB-A No. 2127406.

I claim:

1. A process for the preparation of a compound of formula (1)

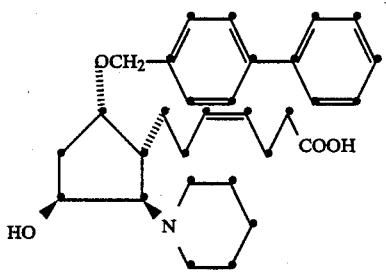

or a salt thereof, which comprises reacting a compound of formula (2)

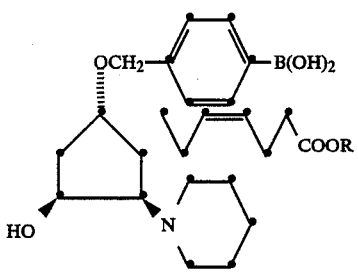

(where R is a hydrogen atom or a $C_{1-6}$alkyl or $C_{7-20}$ aralkyl protecting group) or a salt thereof, to replace the moiety $B(OH)_2$ with a phenyl group, followed where necessary by removal of a $C_{1-6}$alkyl or $C_{7-20}$ aralkyl protecting group and/or by salt formation.

2. A process according to claim 1 in which replacement of the moiety $B(OH)_2$ in formula (2) by a phenyl group is effected with a compound of formula (3)

PhX    (3)

where Ph represents phenyl and X represents a conventional leaving group.

3. A process according to claim 2 in which compounds of formulae (2) and (3) are reacted wherein X represents a halogen atom.

4. A process according to claim 3 in which the coupling reaction is carried out in the presence of a transition metal catalyst in a solvent containing a base.

5. A process according to claim 4 in which the transition metal catalyst is $(Ph_3P)_4Pd$.

6. A process according to claim 5 in which the solvent is an ether.

7. A process according to claim 5 in which the base is aqueous sodium carbonate.

8. A process as claimed in claim 1 which comprises the steps of (i) reacting a compound of formula (2) in which R is a $C_{1-6}$alkyl or $C_{7-20}$ aralkyl group or a salt thereof to replace the moiety $B(OH)_2$ with a phenyl group to form the ester (5)

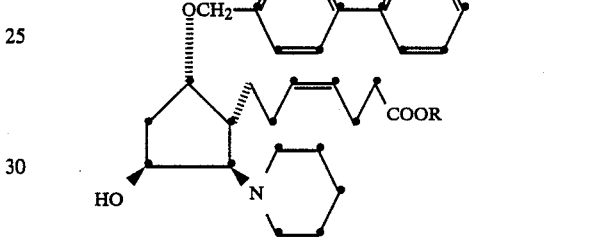

or a salt thereof (where R is a $C_{1-6}$alkyl or $C_{7-20}$aralkyl group) and (ii) hydrolysing the ester (5) or a salt thereof to obtain the acid of formula (1) and optionally treating said acid to obtain a salt thereof.

* * * * *